United States Patent
Lynn et al.

(10) Patent No.: US 9,132,253 B2
(45) Date of Patent: Sep. 15, 2015

(54) ASTHMA RESUSCITATION SYSTEM AND METHOD

(75) Inventors: Lawrence A. Lynn, Columbus, OH (US); Roger Dzwonczyk, Columbus, OH (US); Russell P. Woda, Columbus, OH (US)

(73) Assignee: Lawrence A. Lynn, Columbus, OH (US)

( * ) Notice: Subject to any disclaimer, the term of this patent is extended or adjusted under 35 U.S.C. 154(b) by 904 days.

(21) Appl. No.: 10/080,387

(22) Filed: Feb. 25, 2002

(65) Prior Publication Data

US 2002/0117173 A1    Aug. 29, 2002

Related U.S. Application Data

(60) Provisional application No. 60/270,514, filed on Feb. 23, 2001.

(51) Int. Cl.
*A61M 16/00* (2006.01)
*A61M 16/08* (2006.01)
(Continued)

(52) U.S. Cl.
CPC ....... *A61M 16/0078* (2013.01); *A61M 16/0084* (2014.02); *A61M 16/08* (2013.01); *A61M 16/0833* (2014.02); *A61M 16/0858* (2014.02); *A61M 16/105* (2013.01);
(Continued)

(58) Field of Classification Search
CPC ..................... A61M 16/0048; A61M 16/0051; A61M 16/0057; A61M 16/0078
USPC ............. 128/202.28, 202.29, 203.11, 202.22, 128/204.23, 205.23, 205.13, 205.17, 128/203.12, 205.14, 205.15, 203.28, 128/205.16, 205.11, 204.21; 73/23.3; 434/262, 265, 272, 275; 600/484, 513, 600/523, 529
See application file for complete search history.

(56) References Cited

U.S. PATENT DOCUMENTS 3,898,883 A * 8/1975 Kozak et al. ................ 73/861.33
4,098,271 A * 7/1978 Maddock ................. 128/202.22
(Continued)

FOREIGN PATENT DOCUMENTS

EP          0369506 A1    5/1990
JP          3222855 A     10/2000

OTHER PUBLICATIONS

NEANN Resuscitation Manikins and Training Aids; http://www.neann.com/Training%20Equipment.htm; no date.
(Continued)

*Primary Examiner* — Justine Yu
*Assistant Examiner* — Kathrynn Reilly
(74) *Attorney, Agent, or Firm* — International IP Law Group, PLLC

(57) ABSTRACT

A resuscitation system for the administration of cardiopulmonary resuscitation of asthma patients, and for teaching the cardiopulmonary resuscitation of asthma patients. The invention includes a deflatable bag and a gas flow channel connected with said bag, for connection with an indwelling endotracheal tube so that gas can flow from the bag into the patient and from said patient through said flow channel, an exhalation port in flow connection with said flow channel and an indicator mounted adjacent said system for detecting expiration flow and/or pressure within at least one of said flow channel and exhalation port to detect inadequacy in the expiratory component of ventilation during CPR and to train healthcare workers in the emergency ventilation of severe asthmatic patients in the field and emergency room.

20 Claims, 6 Drawing Sheets

(51) Int. Cl.
*A61M 16/10* (2006.01)
*A61M 16/20* (2006.01)
*A61M 16/12* (2006.01)

(52) U.S. Cl.
CPC .......... *A61M 16/125* (2014.02); *A61M 16/208* (2013.01); *A61M 16/1065* (2014.02); *A61M 16/12* (2013.01); *A61M 2016/0021* (2013.01)

(56) References Cited

U.S. PATENT DOCUMENTS

| | | | |
|---|---|---|---|
| 4,331,426 A * | 5/1982 | Sweeney ........................ | 434/265 |
| 4,395,919 A | 8/1983 | Peters | |
| 4,733,570 A | 3/1988 | Peters | |
| 4,850,876 A * | 7/1989 | Lutaenko et al. ............. | 434/265 |
| 4,945,918 A * | 8/1990 | Abernathy .................... | 600/532 |
| 5,038,621 A | 8/1991 | Stupecky | |
| 5,163,424 A * | 11/1992 | Kohnke .................... | 128/205.13 |
| 5,195,896 A * | 3/1993 | Sweeney et al. ............. | 434/265 |
| 5,279,289 A * | 1/1994 | Kirk ......................... | 128/205.23 |
| 5,286,206 A * | 2/1994 | Epstein et al. ................ | 434/265 |
| 5,330,514 A * | 7/1994 | Egelandsdal et al. ......... | 434/265 |
| 5,375,592 A | 12/1994 | Kirk et al. | |
| 5,456,249 A * | 10/1995 | Kirk ......................... | 128/205.13 |
| 5,468,451 A | 11/1995 | Gedeon | |
| 5,480,611 A | 1/1996 | Mills et al. | |
| 5,486,151 A * | 1/1996 | Bergmann et al. ................ | 483/1 |
| 5,487,382 A | 1/1996 | Bezicot | |
| 5,487,731 A | 1/1996 | Denton | |
| 5,497,767 A * | 3/1996 | Olsson et al. ............ | 128/205.13 |
| 5,517,985 A | 5/1996 | Kirk et al. | |
| 5,557,049 A * | 9/1996 | Ratner ............................ | 73/715 |
| 5,591,130 A | 1/1997 | Denton | |
| 5,598,839 A * | 2/1997 | Niles et al. ............... | 128/205.23 |
| 5,664,563 A * | 9/1997 | Schroeder et al. ....... | 128/204.25 |
| 5,679,884 A | 10/1997 | Kirk | |
| 5,728,066 A * | 3/1998 | Daneshvar ................. | 604/96.01 |
| 5,749,358 A * | 5/1998 | Good et al. ............. | 128/205.23 |
| 5,772,442 A | 6/1998 | Lampotang et al. | |
| 5,885,084 A * | 3/1999 | Pastrick et al. ............... | 434/265 |
| 5,937,852 A | 8/1999 | Butler et al. | |
| 5,941,710 A | 8/1999 | Lampotang et al. | |
| 5,975,078 A * | 11/1999 | Pauley ..................... | 128/205.23 |
| 6,058,933 A * | 5/2000 | Good et al. ............. | 128/205.13 |
| 6,123,075 A * | 9/2000 | Kirk ......................... | 128/205.13 |
| 6,155,257 A * | 12/2000 | Lurie et al. ............... | 128/204.23 |
| 6,174,295 B1 * | 1/2001 | Cantrell et al. .................. | 601/41 |
| 6,296,490 B1 * | 10/2001 | Bowden ........................ | 434/265 |
| 6,342,039 B1 | 1/2002 | Lynn et al. | |
| 6,427,687 B1 * | 8/2002 | Kirk ......................... | 128/203.11 |
| 6,435,183 B1 * | 8/2002 | Farman .................... | 128/204.25 |
| 6,609,016 B1 | 8/2003 | Lynn | |
| 6,760,608 B2 | 7/2004 | Lynn | |
| 7,398,115 B2 | 7/2008 | Lynn | |
| 8,152,732 B2 | 4/2012 | Lynn | |
| 2007/0129647 A1 | 6/2007 | Lynn | |

OTHER PUBLICATIONS

CPR Medical Devices, Inc.; The Oxylator® EM-100; http://www.eprmedic.com/intro.htm; no date.
Open Form Abstracts in Respiratory Care; vol. 35, No. 11, pp. 1114; Nov. 1990.
Braschi Valve; Illustration; 2 pages.
Lung Simulators; http://www.michiganinstruments.com/various.htm; 2 pages; no date.
Laerdal Brochure; "Bringing Simulation to Life";2001.
Woda et al; "The ventilatory effects of auto-positive end-expiratory pressure development during cardiopulmonary resuscitation"; Crit. Care Med; vol. 27, No. 10; 1999; pp. 2212-2217.

* cited by examiner

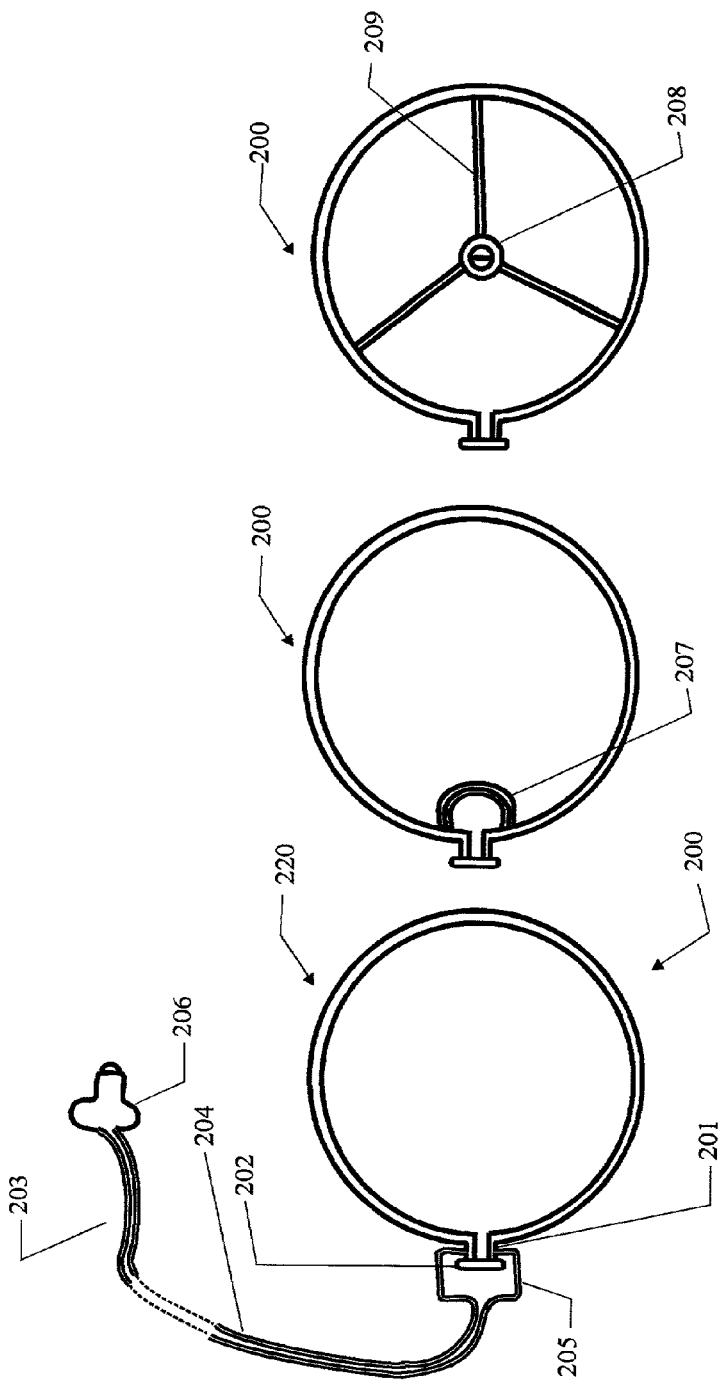

ASTHMA RESUSCITATION SYSTEM AND METHOD

CROSS-REFERENCES TO RELATED APPLICATIONS

This application claims the benefit of U.S. provisional Application Ser. No. 60/270,514, which was filed Feb. 23, 2001, the disclosure of which is incorporated herein by this reference.

BACKGROUND AND SUMMARY OF THE INVENTION

This invention relates to medical resuscitated bags for ventilation during cardiopulmonary resuscitation and during patient transport and to cardiopulmonary resuscitation training systems.

The development of air trapping or auto-peep during patient ventilation with resuscitation bags operated by the hands of a nurse, respiratory therapist, or physician represents an important problem. A recent study published by the present inventors in Critical Care Medicine shows that severe air trapping is induced by these bags in patients with obstructive lung disease or asthma. This air trapping causes a rise in positive end expiratory pressure (PEEP) in the chest. The pressure in the chest becomes more and more positive preventing blood flow back to the heart, this can result in a fall in cardiac output which can result in shock and severe patient injury and death. This is especially important when associated with blood volume depletion as with trauma or sepsis. In such a case any increase in PEEP within the chest can potentially decrease the resuscitation potential of a patient.

This rise in pressure is often insidious and occurs in slow incremental amounts with each breath until a new steady state is reached with substantial mean alveolar pressure and PEEP levels about which the operator is entirely unaware. The failure to achieve adequate cardiac output in this situation is often attributed to other causes and may be perceived as a generic "pulseless electrical activity" (PEA) for which inappropriate and potentially dangerous cardiac stimulating pharmacological therapy may be urgently applied by ACLS protocol. Failure to correct this hidden pressure build up within the chest cavity during CPR can result in resuscitation failure and death. This is likely to be one of the reasons that the death rate is so high in asthma patients resuscitated by the standard ACLS protocols used throughout the U.S. by emergency rooms and paramedic squads. The ACLS protocol calls for the patient to be bagged at a rate of one breath for every five compressions, which we have shown experimentally, causes severe air trapping and potentially life-threatening PEEP in a large population of patients. One of the present inventors is aware of at least two patients who died as a result of this problem when other doctors and healthcare workers, unaware of the development of Auto-Peep, attempted to apply ACLS protocol to patients who had advanced obstructive lung disease.

For these reasons there has been a long and critical need for a resuscitation bag system and method which can warn the operator when the patient has trapped air or Auto-Peep so that the ventilation rate or volume can be reduced to allow time for the patient to completely exhale. This will allow the pressure to fall within the chest to lower levels allowing sufficient blood return to the heart. In addition there has been a long and critical need for a system and method for providing hands on training of the clinical findings and significance of hyperinflation during CPR.

It is considered important that any new medical resuscitated bag have a low manufacturing cost, as most resuscitation bags are now disposable. The present inventors recognized that it is important that all bags provide an indicator of trapped air both in the field and in the hospital. For this reason it is considered desirable to provide an embodiment of the indicator which is inexpensive and disposable, so that comprehensive implementation is easily achieved.

The present invention comprises a simple resuscitation bag system including a bag having a port for connection to an oxygen source, a conduit with a terminal for connection with an indwelling endotracheal tube, a one way valve intermediate the bag and the terminal to prevent exhalation back into the bag, an exhalation port, and an indicator connected with said system which indicates when pressure and/or airflow from the patient is present after the inhalation has been completed. The indicator allows the recognition of trapped air during bagging so that survival in patients with obstructive lung disease or low blood volume can be improved during CPR. The pressure or flow indicator can be adjacent the bag or adjacent the connecting tubing between the patient and is preferably mounted adjacent with or is integral with the exhalation port. The indicator can be a simple pressure or flow sensing device such as a disposable pneumotachometer or other type of flow and/or pressure sensor as are well known in the art. The indicator is sized and configured to provide automatic visual or auditory indication of persistent airflow or pressure during exhalation so that the exhalation does not need to be stopped or any changes made by the operator to identify the presence of persistent flow which can indicate air which will be trapped if the bag in manually compressed before the exhalation process in completed. In the preferred embodiment the indicator is a simple disposable elastomeric member which is mounted adjacent the exhalation conduit of a resuscitation bag or endotracheal tube and which is positioned so as to be readily visible to the operator and which deforms in the presence of flow and/or pressure such that the presence of said deformation can be used to indicate the persistence of flow and/or pressure during exhalation after a manual inflation of the lungs by the bag system.

In another preferred embodiment of the invention, the indicator consists of an auditory port located through the side of the exhalation port to which a listening device such as a disposable esophageal stethoscope is connected. The esophageal stethoscope is comprised of a long flexible tube with a standard fitting, such as a Luerlok fitting, at one end and an earpiece at the other end, a design well known in the art. The earpiece is placed in the ear of the operator/rescuer. Gas flow is detected by the sound of gas flowing through the exhalation port and into the ambient environment. A small protuberance is located on the interior wall of the exhalation port and in proximity to the auditory port to enhance the level of sound. In a further improvement to this embodiment, a whistle is mounted on the interior of the exhalation port and in proximity to the auditory port. The whistle generates a sound in the human auditory range of frequencies as gas flows through it. Gas flow is then detected, after a manual inflation of the lungs by the bag system, by the sound generated by the whistle.

One reason that air trapping is poorly recognized in the field is that advanced cardiac life support education does not teach well the physiologic issues and clinical findings relating to this important adverse process. For example PDA is described as caused by the "5 Hs". However, the present inventor realized that a "$6^{th}$ H" (hyperinflation) should be included as one of them to teach paramedics, nurses, EMTs and physicians this important cause of hypotension and PDA during ventilation and CPR respectfully. In fact it is critical to include hyperinflation because it likely the most common unrecognized cause of PDA in patients with asthma or advanced COPD.

Upon this realization, a present inventor developed a system and method for teaching healthcare workers to recognize hyperinflation during resuscitation. This system and method is particularly useful when applied with the Bag system disclosed supra. Resuscitation manikins commonly known as "Annie" are in wide use for cardiopulmonary resuscitation (CPR) and advanced cardiac life support training. These devices have a simulated pharynx and trachea, which connects with bilateral airways, which extend to two inflatable elastic bags which simulate the lungs. With the conventional Annie, these airways and trachea are wide open such that the "lungs" deflate at a relatively rapid rate so that the condition of expiratory obstruction is not simulated. The user, often learning how to manually ventilate a patient for the first time, can develop a false sense of the speed of exhalation and is not provided with any simulation which approximates the high risk and often fatal state of airway obstruction and hyperinflation associated with asthma (especially pediatric asthma). They become comfortable with bagging at conventional rates not recognizing the sever risk of hyperinflation in certain patient subgroups. Conventional Annie therefore may actually mislead these healthcare workers into a false understanding of the real complex physiology of bagging during resuscitation. In particular, with pediatric asthma it is easy to over inflate the smaller lungs so these patients are at grave risk so that the false sense of free exhalation provided by Annie is a dangerous deficiency. Indeed death from pediatric asthma and adult asthma after incubation is quite high and this would other wise seem surprising since asthma itself is generally a reversible disease.

According to the present invention a means for inducing airflow restriction and particularly expiratory airflow restriction is applied to at least a portion of the flow path intermediate the resuscitation bag and the "lungs" of the resuscitation manikin to reduce at least the rate of exhalation such that the rate of deflation at least one of the "lungs" is decreased to simulate resuscitation of a patient with asthma or advanced COPD. A fixed restrictor, or a restrictor which provides a variable and selectable degree of restriction to flow within the flow channel, can provide the flow restriction. The flow restrictor can be provided with along the tubing of the resuscitation bag intermediate the bag and the endotracheal tube-connecting member as a fixed member, or can be an accessory which is selectively engaged or attached with the flow path when simulation of airway obstruction is desired. In one embodiment the flow path along or adjacent the endotracheal tube can be provided with a flow restrictor. In the presently preferred embodiment the flow restrictor is provided along or adjacent at least one of the airways and preferably selectably restricts flow along one or both airways between one or both lungs and the resuscitation bag and is preferably hidden from the operators view so that the presence of airflow restriction The flow restrictor can be a provided by providing small diameter trachea and/or airways along their entire length, a region of narrowing in the diameter of the trachea and/or airways, and/or by providing an obstructing member such as a valve within or along the airway, which can be more restrictive during inhalation than exhalation. In one presently preferred embodiment the narrowing is constructed to dynamically enlarge during inspiration and reduce in size during exhalation. A fixed restrictor or a restrictor, which provides a variable and selectable degree of restriction to flow within the flow channel, can provide the flow restriction. In one embodiment the flow restrictor is at least one elastic ring, which compresses a segment of the flow channel. In another embodiment the restrictor is a fixed narrowing of a segment of the flow channel.

The provision of a manikin simulating the physiology of asthma with basic elastic or inelastic airway narrowing (as by the of a simple inelastic ring or elastic ring inserted in, mounted with and/or integral with the airflow path. Both narrow elastic airways, or a fixed narrowing or valve within the airways has the advantages of simplicity and low cost. For example, one low cost embodiment includes an elastic ring (such as a thin wall elastic silicone, poly-isoprene or latex rubber band ring of approximately 2-4 cm in width having a internal diameter in its resting state less than that of the airway) mounted along the airway. The band is mounted so that it can be selectively movable along the airway from a first position wherein the ring is mounted over rigid portion of the airway (so that no airway narrowing or restriction to airflow is provided) to a second position along a compressible portion which is compressed by the elastic force of the ring to narrow the compressible portion and provide elastic flow restriction which is greater during exhalation (when the internal pressure within the airway to elastically distend the ring is less) than during resuscitation bag or ventilator generated inspiration, when the internal airway pressure to distend the ring is greater).

In one the presently preferred embodiment the airflow restrictor is a balloon, which provides variable compression to at least a segment along the flow channel. Preferably two elastic balloons are provided, such as thin walled silicone balloons, each containing a soft collapsible segment of an airway. The balloons are selectively each connected to a separate air vent (which can for example be a pilot tube of the type used for endotracheal tube or tracheotomy tube cuffs). The air vents preferably are connected with a valve (which can for, example, be a syringe the type of valve activated by a luer tip of a syringe as are widely used with the pilot tubes of endotracheal tubes), the tube is further connectable and/or connected with a pump which can be used to selectively inflate the balloon (such as a syringe or, in another example, the hand bulb pump (with a valve) of the type commonly used for blood pressure cuffs). The valve, preferably selectively allows air to escape from the balloons after inflation but which can be closed to allow prolonged inflation as during manikin training sessions, which the present inventor calls "advanced ventilation life support" (AVLS) teaching adult and pediatric asthma resuscitation and ventilation. The pilot tube or vent can be a single tube which bifurcates containing at least one valve between the air vents and the pump so that the pump can selectively inflate one or both balloons to provide selective flow restriction to one or both airways. In another embodiment each vent is connectable with a separate or removable pump (such as a syringes). In one embodiment each with different pressure gauges so that each balloon can be readily inflated to the same or different pressures. In a further embodiment the lungs of the manikin are modified to simulate the effect of loss of elastic recoil of the lungs on the development of dynamic hyperinflation (air trapping) during CPR. An accessory set of replacement lungs with a low elasticity recoil ("emphysema lungs") is provided which can be applied to replace the more elastic lungs. This modification provides for the opportunity for teaching and improved recognition of the significance of expiratory time when ventilating patients with advance emphysema especially when combined with airway narrowing.

It is the purpose of the present invention to provide a portable manual bag for patient ventilations (and especially emergency ventilation in the field), which provides an indicator of air trapping during ventilation so that children and adults with asthma and/or advanced chronic obstructive lung disease (COPD) have a better chance of survival during resuscitation and ventilation.

It is further the purpose of this invention to provide a resuscitation manikin for advanced cardiopulmonary resuscitation training, which has a means to simulate the pathophysiology of asthma, emphysema, and airway narrowing (including elastic airway narrowing) so that healthcare workers can recognize air trapping during CPR to improve survivability of this group of patients.

It is further the purpose of the present invention to provide a resuscitation bag with an indicator of air trapping in combination with a resuscitation-training manikin having at least heightened airway resistance such that air trapping occurs during normal CPR rates of ventilation so that health care workers can learn to recognize air trapping during routine CPR training.

BRIEF DESCRIPTION OF THE DRAWINGS

These, as well as other objects and advantages of this invention, will be more completely understood and appreciated by careful study of the following more detailed description of the presently preferred exemplary embodiments of the invention taken in conjunction with the accompanying drawings, in which:

FIG. 6a is a cross-sectional view of the expiration port showing the auditory port with standard fitting;

FIG. 7 is a cross-sectional view of the expiration port showing the auditory port and small protuberance;

FIG. 8 is a cross-sectional view of the expiration port showing the auditory port and a whistle located in the lumen of the expiration port;

DETAILED DESCRIPTION OF THE INVENTION

Figure 1:
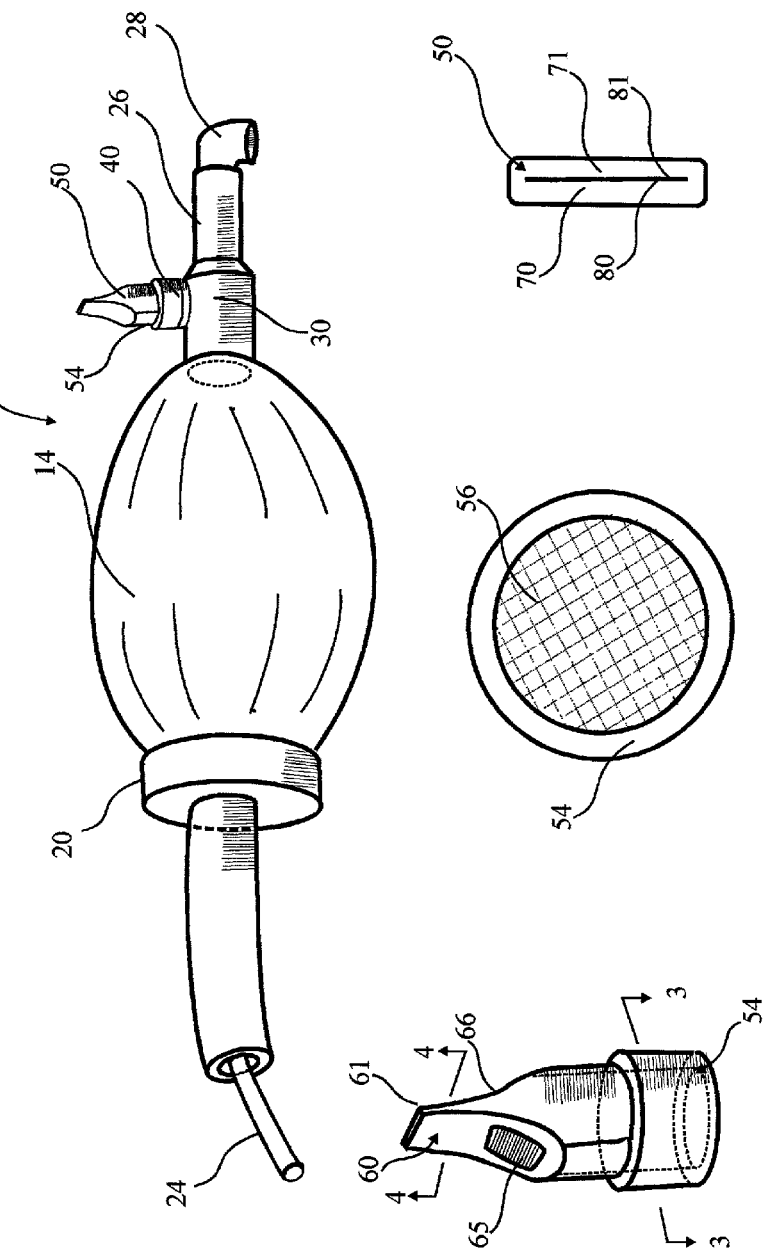
FIG. 1 is a perspective view of a medical resuscitation bag according to the present invention.
Figure 4:
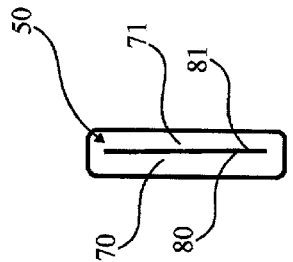
FIG. 4 is a cross-sectional view through lines 4-4 of FIG. 2 showing the indwelling filter.
Figure 3:
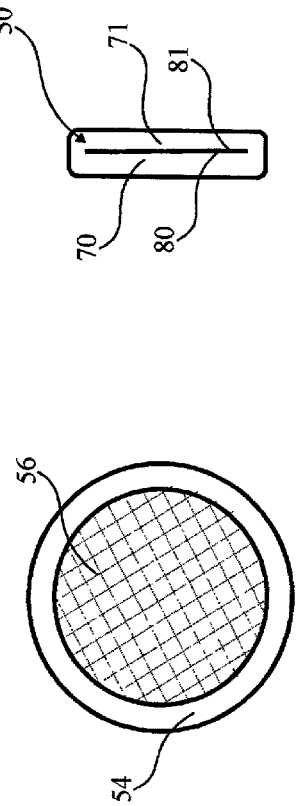
FIG. 3 is a cross-sectional view through lines 3-3 of FIG. 2.
Figure 2:
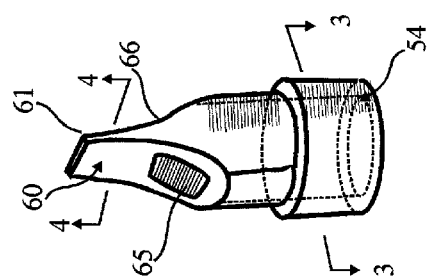
FIG. 2 is a perspective view of the filtered exhalation flow indicator according to the present invention.

FIG. 1 shows the disposable manual resuscitation bag system 10 including a conventional disposable resuscitation bag 14 having an end 20 for connection with an oxygen source 24, a distal tube 26 receiving a terminal arm connector 28 for connection with an indwelling endotracheal tube or mask (not shown). The system includes a proximal valving portion 30 which includes and a flow directing valve system 30 (as are known and in wide use in the art) intermediate the connector 28 and the bag 14. The system 10 further includes an exhalation port 40 and a flow indicator 50 mounted about the exhalation port 40. The flow indicator 50 includes flexible mounting tube 54 which includes a microbiologic filter 56. The tube is sized to be place over the exhalation port 40 and a projecting pair of duckbill walls 60 and 61 extending to ends 70 and 71. The walls 60 and 61 are thin (in the range of 1 mm) and include opposing faces 80 and 81 abutting one another. The walls 60 and 61 are thin so that they open with minimal pressure or flow. The duckbill walls 60 and 61 are preferably comprised of flexible and elastic material such as silicone. For example, the walls can be comprised of the same material used to form the walls of the one way valve used in the SIMS Portex "1st Response Manual Resuscitator" and can be for example approximately 0.5 mm in width. The ends 70 and 71 can be colored bright white on the outside and the opposing faces 80 and 81 can be colored, for example bright blue or red. This allows any opening in the duckbill to be better visualized by the operator. The walls 60 and 61 also include opposing regions 65 and 66 of very thin elastomer (as 0.25 mm or less) with can be lax in this region so that this region is very flexible and balloons outward when flow strikes the region or when pressure is present within the duckbill.

In operation the terminal is connected to the endotracheal tube and the bag in manually compressed and air enters the patients lungs. When the compression on the bag is released, the patient exhales through the exhalation port. The flow of gas through the port caused the duckbill ends 70 and 71 to separate. This separation is easily visualized and makes the operator aware that exhalation flow is continuing. By inference, the presence of exhalation flow means that the alveolar pressure is greater than the atmospheric pressure and that air is still trapped. The operator can then delay the next breath to prevent further augmentation of the pressure within the chest. Of course some patients take so long to exhale that the next breath will need to occur before the flow stops but here the indicator still provides important information since such patients are at great risk for the development of AUTO PEEP which can cause pulseless electrical activity and hypotension. The presence of long flow times identifies these patients at risk so that other actions (such as lower tidal volumes, more rapid inhalation, or intravenous volume expansion can be initiated. The duckbill flow indicator thereby provides an immediate inexpensive disposable means for showing the presence of expiratory flow which can be used to provide more physiological correct manual ventilation in patients, especially those with obstructive airways disease or low blood volume.

Other elastomeric configurations can be provided which deform in the presence of flow. A whistle can be added which indicates flow by an auditory indicator. The visual presence of flow can be provided and even obtained quantitatively by providing a wheel, which rotates in the presence of flow. (Simple quantitative wheel based flow sensors are known in the art). At least a portion of the elastomer can be transparent and a carbon dioxide detector can be added adjacent or within the duckbill.

Alternatively a flow or pressure sensor can be placed intermediate the endotracheal tube and the bag and may be connected with, or integral with the connection terminal of the bag. In an alternative embodiment a paper or other type of carbon dioxide detector (as are known in the art) can be positioned so that it extends into the atmosphere just beyond the exhalation port or in a position wherein residual carbon dioxide is flushed or otherwise does not remain after exhalation has been completed so that the indicator can provide evidence of the presence of persistent exhaled gas flow.

Figure 5:
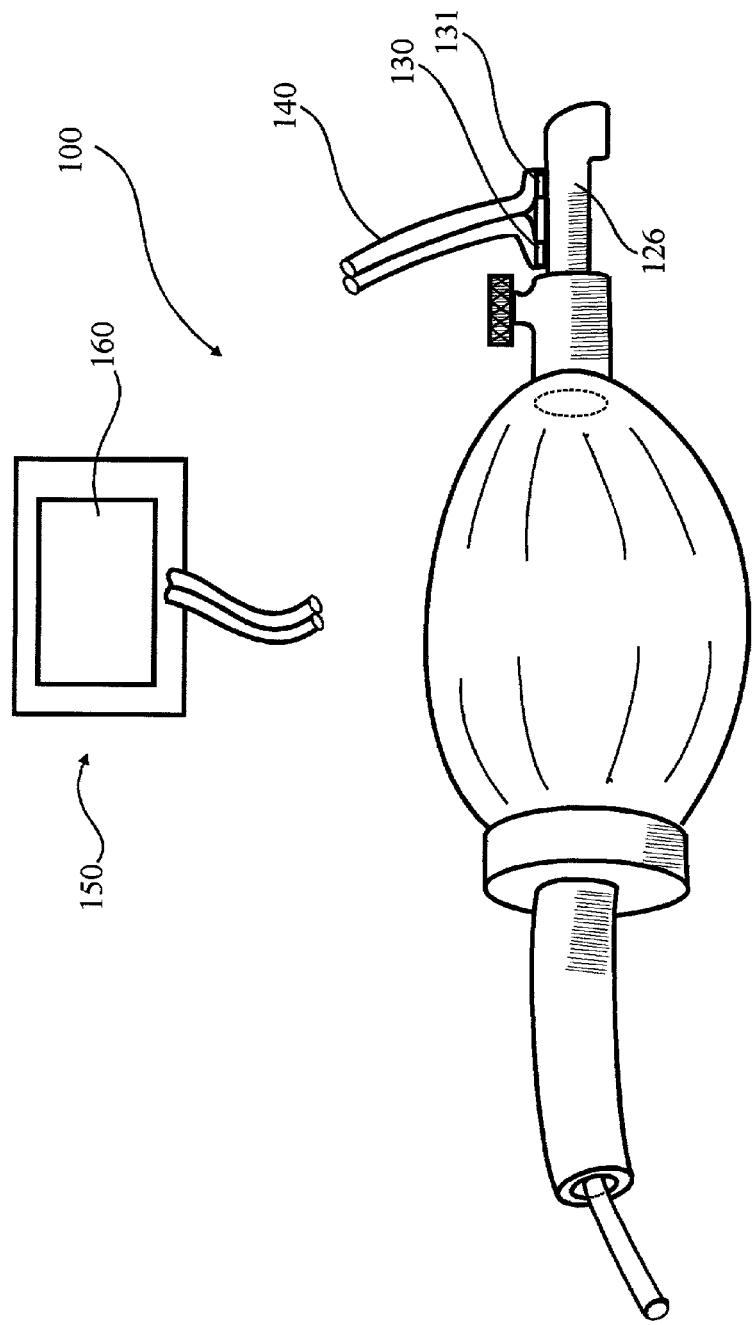
FIG. 5 is a perspective view of another embodiment of the medical resuscitation bag according to the present invention.

In an alternative design shown in FIG. 5 a disposable manual resuscitation bag system 100 which is of similar configuration to the embodiment of FIG. 1 but in this embodiment the flow sensing is provided by providing a modification of distal tube 26 of the embodiment of FIG. 1 to provide a new distal tube 126 which functions as a pneumotachometer flow tube. The tube 126 includes separated spaced ports 130 and 131 connected to disposable pressure tubing 140 (Shown broken) for connection with a pressure sensor and a microprocessor 150 to provide real-time output on display 160 of the inspiratory and expiratory flow characteristics and the inspiratory and expiratory flow ratio so that auto peep can be optimally controlled as well as identified. The tube 126 has a known resistance to flow and the ports 130 are separated by a known resistance so that flow can be calculated as is well known in the art for the operation of pneumotachometers. Alternatively other pneumotachometer designs can also be incorporated into or with the distal tube 126. However this presently preferred design is advantageous over designs which incorporate the insertion of a disposable pnumotachometer into the line between the endotracheal tube and the distal tube 26 of FIG. 1 in that it can be provided with a lower manufacturing cost and it obviates the need for the insertion of an additional length of cumbersome flow tubing and helps to reduce the disconnect potential which is associated with the addition of accessory tubing.

In another embodiment an auditory indicator is provided. If desired to obtain addition length of resistance tube without extending the length of the distal tube 126 outside the bag, the proximal portion of the distal tube 126 can be elongated within the bag. The pressure waveforms can be recorded with a high fidelity recording sampling for example at 25 Hz. This waveform can then be analyzed for recognition of the pressure waveforms from chest compression and the determination of their magnitude (which can be for example defined by the deflection amplitude). The real-time output and stored time series of these pressure waveforms can be used to monitor and review reflect the effectiveness of the chest compressions to vary intrathoracic pressure and the manner in which CPR was derived (since both chest compressions and ventilation will be reflected in the time series as well as any gaps in each). Using, for example, the digital pattern recognition technology described in Provisional patent application No. 60/291,691 entitled "System an method for identification of dynamic patterns of interaction between corresponding time series" and Provisional application No. 60/291,687 entitled "Microprocessor System for the analysis of physiologic and financial datasets" (the disclosure of each of these applications is incorporated by reference as if completely disclosed herein), these air pressure and flow time series can be integrated and compared along with the EKG, chest wall impedance, pulse, oximetry (pulse output and saturation), the exhaled carbon dioxide and other derived time series to provide a comprehensive relational analysis of the resuscitation process where the nurse inputs the times of selected drug administrations and interventions as from a touch pad selection option. This system can provide real-time prompts indicating the potential need for certain medications or warning of potential deleterious inadequacies in compression amplitude, timing or as a function of prolonged gaps which sometimes occur during CPR (such as during transport or while examining EKG strips). The digital pattern recognition technology described in the aforementioned applications provides the ability to output to the operator of the asthma resuscitation system the inspiratory time, the inspiratory to expiratory ratio, the presence of residual flow at the onset of inspiration, the amplitude and upstroke slope of chest compression pressure, as reflected in the in the compression waveform through the airway. The system also allows for filtering of the chest compression pressure waveforms (which produces a pattern of very rapid brief reciprocation, with a rapid return to baseline) from the ventilation waveforms (which comprise much slower reciprocation) if desired to improve flow calculations. The central processor integrating these signals can thereby output information, which allows optimization of chest compressions and ventilation. In addition, the return of cardiac contraction can be detected and identified through the airway using the pressure monitored other flow monitor according to the present invention. With the digital pattern recognition technology (as described in the aforementioned patent applications), these oscillations can be correlated with the EKG signal to confirm the reversal of electromechanical dissociation. The recognition of cardiogenic oscillations through the airway is known in the art. The present invention can provide a real-time output indicating to the rescuers that cardiac contraction has returned (as in conditions such as PEA). The magnitude of these cardiac oscillations can be used to indicate (grossly) the magnitude of the return of cardiac contractility so that blood pressure and other assessments of the effectiveness of cardiac contractions can be quickly evaluated by the team open notification by the monitor of the invention that cardiac oscillations are present. In the alternative the monitor upon detecting the return of cardiac oscillations can immediately trigger, for example, a non-invasive blood pressure monitor for the measurement of blood pressure to corroborate the return of cardiac contractility.

FIG. 6a shows an auditory flow indicator. In its simplest form (FIG. 6a), the auditory flow indicator 200 consists of an auditory port 201 extending through the sidewall of the exhalation port 220 downstream from any antibacterial filter and terminated on the exterior by a standard fitting 202, such as a Luer lock fitting. A listening device 203, such as a disposable esophageal stethoscope, is connected to the fitting. The esophageal stethoscope is comprised of a long flexible narrow-diameter plastic tube 204 with a standard fitting 205 compatible with the fitting terminating the auditory port, such as a Luer lock fitting, at one end and an earpiece 206 at the other end. This design is well known in the art and commercially available. In operation, the earpiece is placed in the ear of the operator/rescuer.

In a further improvement in the design (FIG. 7), an irregular protuberance 207 is located immediately adjacent to the auditory port 201 on the interior sidewall surface of the exhalation port 220, and protrudes out into the exhalation port 220 for the purpose of generating localized turbulent flow of gases passing through the exhalation port and thereby enhancing the generation of sound due to gas flow.

In yet another improvement in the design (FIG. 8), small whistle 208 is located in the center of the exhalation port 220 and secured by several thin brackets 209 extending from the whistle 208 to the interior sidewall of the exhalation port 220 for the purpose of generating a sound in the human auditory range of frequencies as exhaled gas flows through the exhalation port and through the whistle. It is understood that the whistle 208 can be any of a variety of designs, including but not limited to a reed whistle, a rotating whistle or other whistle. Its main design feature must be that it produces sound when gas flows through or past it and that it is sensitive to low gas flow levels.

In operation, the bag is manually compressed, forcing gas into the patient's lungs. When the compression on the bag is released, the patient exhales through the exhalation port 220. Any turbulent flow in the circuit generates a sound in the human auditory frequency range that propagates through the circuit, into the exhalation port 220, through the auditory port 201 extending through the sidewall of the exhalation port 220, through the listening device 203 and then detected by the operator/rescuer at the earpiece 206 of the listening device 203. The presence of sound indicates that, during the exhalation phase, gas pressure in the lungs is greater than the ambient atmospheric pressure and that this pressure difference is causing gas flow from the lungs to the ambient environment.

The small protuberance 207 and the whistle 208 both enhance the generation of sound. The protuberance 207 will cause the gas to flow turbulently in its vicinity thus generating sound that will travel through the listening device 203 to the operator/rescuer. The whistle 208 will, be definition, generate sound in the human auditory frequency range as gas flows through or past it. That sound will travel through the listening device 203 to the operator/rescuer. Again, the presence of sound indicates that gas is flowing from the lungs to the ambient environment due to a pressure difference between the lungs and the ambient atmosphere.

Figure 9:
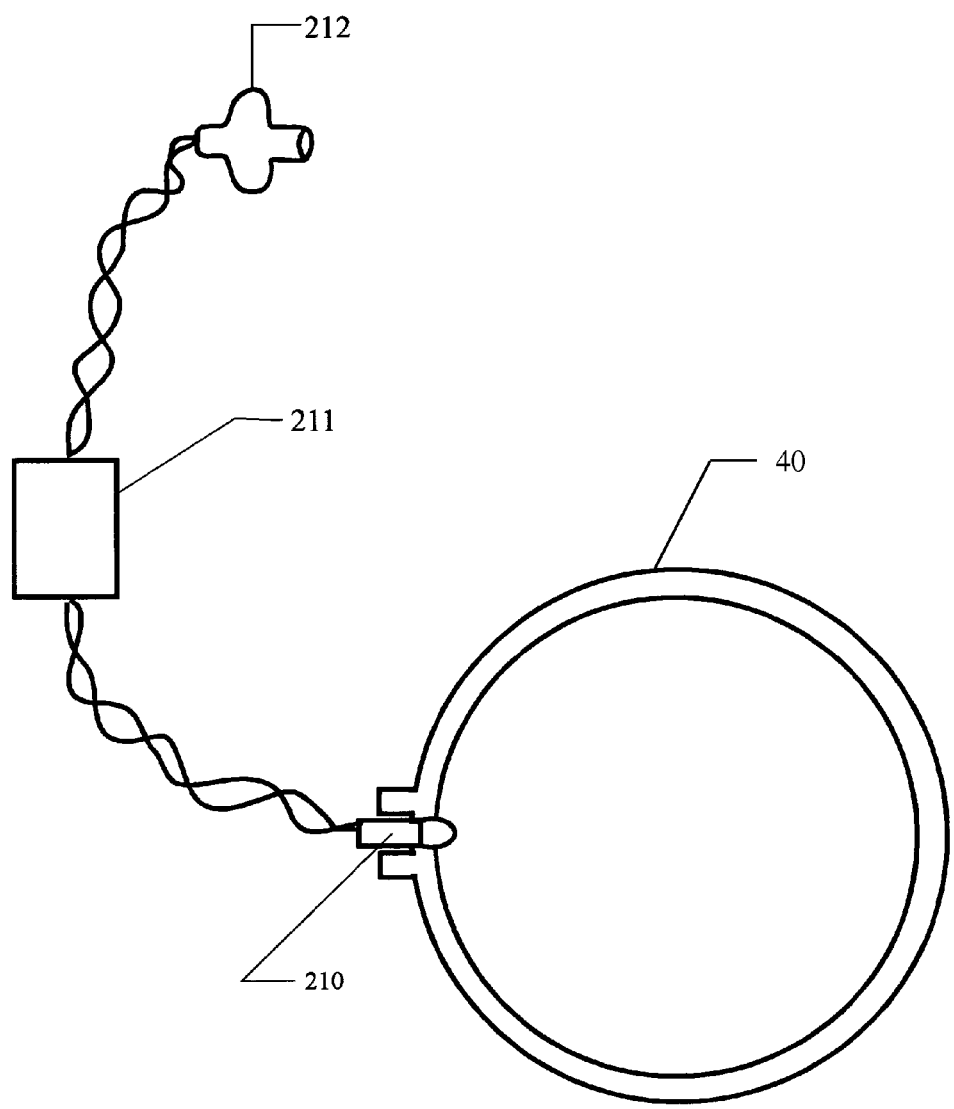
FIG. 9 is a cross-sectional view of the exhalation port showing the auditory port and a small microphone electrically connected to an amplifier/signal processor and, in turn, to an earphone.

In a further enhancement to the auditory flow detector (FIG. 9), the listening device is comprised of a small microphone 210 located in the auditory port 201 in the sidewall of the exhalation port 220 and extending just into the exhalation port. The microphone is connected electrically, in turn, to a single-use battery-operated amplifier/signal processor 211 and a miniature earphone 212, similar to a portable radio earphone that is placed in the ear of the operator/rescuer. In this configuration, sound produced by gas flow from the lungs to the ambient environment, either by turbulent flow or a whistle, is amplified and processed, predominantly by filtering and/or frequency shifting/enhancing, so as to maximize the sensitivity of the auditory flow indicator to exhalation gas flow and, at the same time, minimize ambient, non-gas flow related sounds. In this configuration, further signal processing could produce a signal that activates a light-emitting diode in the presence of gas flow and thereby add a visual component to the device.

Figure 10:
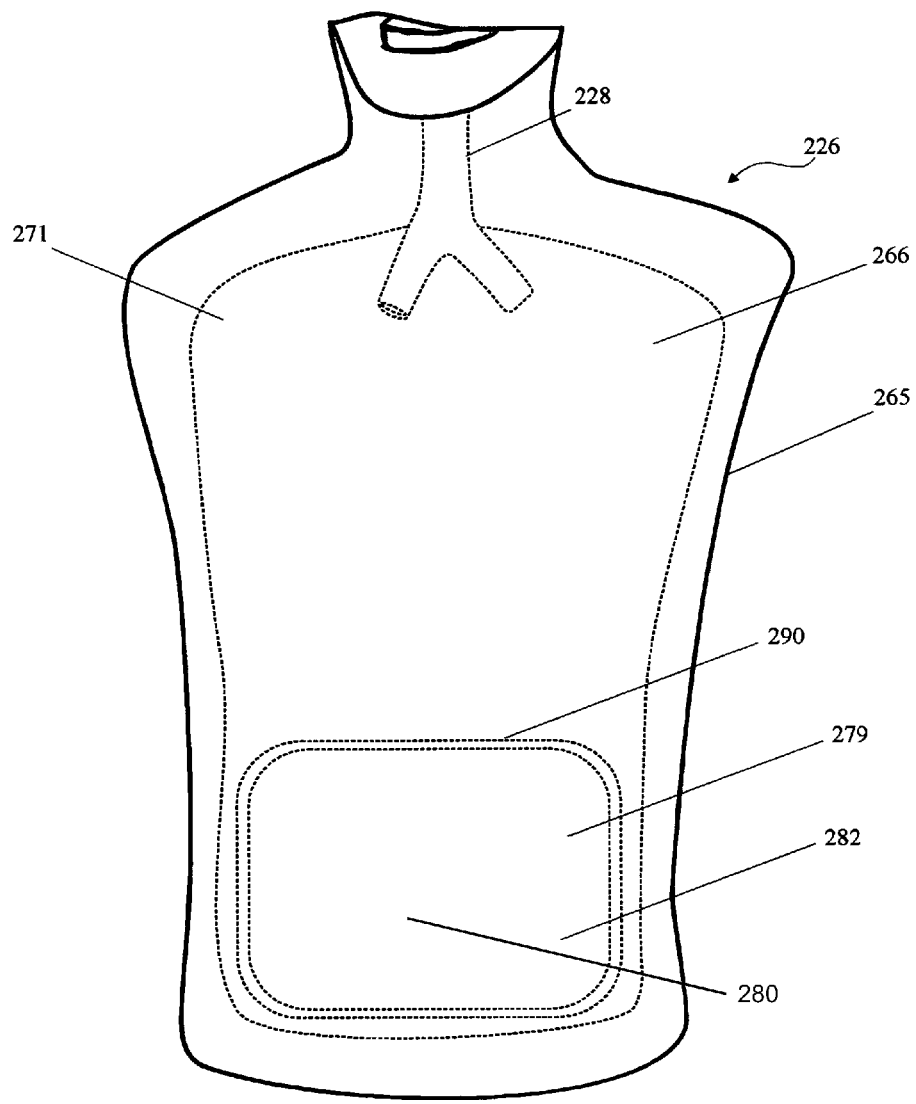
FIG. 10 shows a resuscitation manikin "Annie" used for training of CPR, that has been modified according to an embodiment of the invention.
Figure 11:
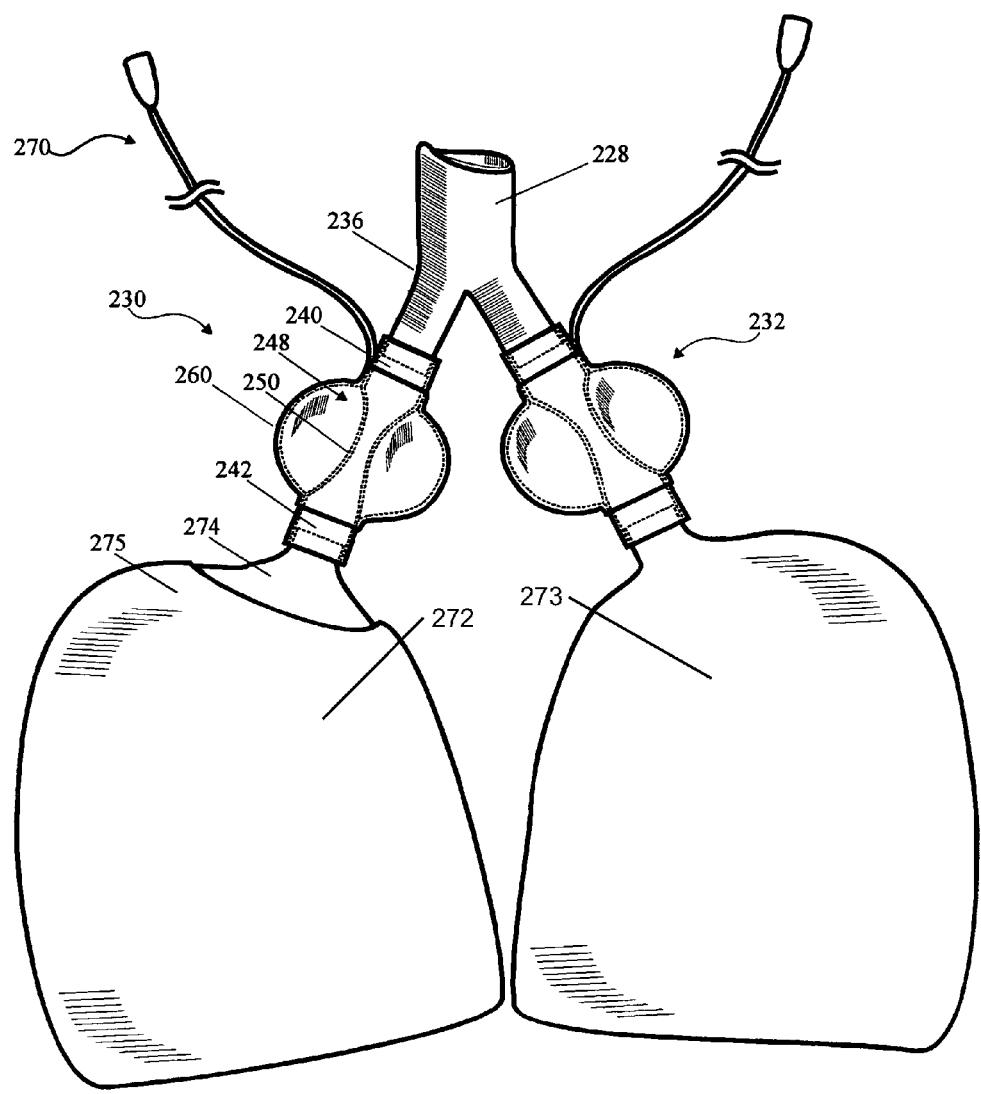
FIG. 11 is a perspective view of a presently preferred embodiment of selectable flow restrictive airways, for use with manikins, to provide an "Asthma Andy" especially for teaching adult and pediatric asthma resuscitation and ventilation.

FIG. 11 shows the asthma resuscitation training system, which can be used in combination with the asthma resuscitation system described supra to optimize experience with difficult ventilation during resuscitation cases in the field, emergency room and hospital. The bifurcated rigid trachea 228 of the asthma resuscitation manikin 226 of FIG. 10 with bilateral variable resistance airway tubes 230, 232 connected to the right main stem bronchus 236. The airway tubes 230, 232 are preferably constructed of flexible and elastic polymer such as silicone. The airway tubes 230, 232 will be described for the right airway tube 230 since they are preferably identical to minimize manufacturing cost. The airway tube 230 includes a proximal flexible region 240 and a distal flexible region 242 shown sized for interference attachment to the main stem bronchus tube 236. The airway tube 230 further includes a flexible resistance region 248 with a deflectable wall 250, which is also preferably elastic. The region 248, can, as shown, be circumferential or can be comprised of thin opposing flat or outwardly rounded sections of opposing walls of the elastic airway tube 230 along the region 248. The variable resistance region 248 of the airway tube 230 has a surrounding balloon 260, which is preferably bonded and/or integral with the airway 230 as is known with silicone cuffs or balloons of endotracheal tubes. (Alternatively the balloon can be fashioned with a tubular passage through it to receive the airway with an elastically deflectable region mounted within the balloon). The balloon has a pilot tube 270 (which can be of the type known in the art for endotracheal tubes) for connection with a syringe (not shown) having volume indicators so that a selected volume can be injected into the balloon (after confirming deflation). Alternatively a bulb inflator (not shown) having a pressure gauge (as are commonly used to provide pressure monitored inflation of endotracheal tube balloons) can be used. The pilot tube 270 can exit the side or posterior chest wall 271 of the manikin so that the airway resistance can be easily adjusted without opening the manikin 226. The pressure gauge provides a means for the trainer to determine the inflation status of the balloons (and therefore the relative resistance of the airways) without looking at the balloons so that the balloons can be hidden within the chest cavity 266 of the manikins 226 for the trainee during resuscitation simulation training providing an "unknown" variable which the trainee is taught to recognize either by exam or by recognition of persistent action of the expiratory flow indicator of resuscitation bag described supra. A pair of elastic balloons "lungs" 272,273, as is known in the art are be attached to the distal end of the airways 230 and 232. In one embodiment the lungs are conventional lungs used in standard resuscitation manikins and can be comprised of elastic silicone. Alternatively the lungs 272,273 can be provided with a resting volume each near the functional residual capacity of an average human and an inflation pressure volume curve (when in the manikin) which simulates the pressure volume curve of the average human to provide the trainees with a better sense of the feel of normal inflation. In an alternative embodiment especially for use with an open manikin (a manikin with an open lower abdomen as is conventional) the "lungs" have a very thin wall 274, which is easily distensible and only weakly elastic to provide a simulation of emphysema lungs if used alone but a second encasing weakly elastic bag (boot) 275 (shown over one lung) is provided to better simulate the higher compliance and greater elasticity of normal lungs. When emphysema simulation is desired the second casing is removed. As noted, the wall of the lungs 274 and boot 275 are comprised of an elastic and compliant material such as silicone so that an internal pressure within the lung is generated on inflation, which causes passive deflation out the airways after the inflation force, has been relieved. In the preferred embodiment the wall of the lungs 274 (and boot 275, if provided) is only modestly elastically compliant so that, when normal or modestly supernormal inflation occurs the resultant air pressure within the lung generated during passive exhalation is insufficient to overcome the deflection of wall 250 due to the air pressure within balloon 260 so that enhanced airway resistance and reduced flow is present in region 248 during passive exhalation when the balloon is inflated. It can be seen that pressure within the balloon 260 can easily be adjusted to provide a internal inflation volume which provides greater resistance to flow during passive exhalation (where the pressure to displace wall 250 back to enlarge the airway is not controlled by the operator) and active inhalation (where the operator adjusts the bagging force thereby can readily generate high deflection forces to enlarge the airway along region 248.

For additional improved simulation of the clinical findings of air trapping the manikin 226 can be modified to include a separate abdominal cavity 279, which is shown in FIG. 10 and can be provided by a simple compressible and elastic air filled abdominal balloon 280 caudal the chest cavity 266 and below a flexible anterior abdominal wall 282. This provides for anterior displacement of the abdomen wall 282 when the lungs are hyper inflated and press down on the abdominal balloon 280. The upper surface 290 of the abdominal balloon 280 also provides resistance to enlargement of the lungs 230,232 thereby making both the inspiratory pressure and expiratory pressure higher thereby simulating the clinical effects of dynamic hyperinflation during CPR for the trainee. The resuscitation manikin 226 will operate to simulate the clinical conditions of asthma without a sealed chest and abdomen. In one preferred embodiment, the airways 230, and 232 simply replace the airways of conventional resuscitation and/or intubation manikin to provide the simulation for teaching. However, as shown, the manikin 226 is provided with the provision of a sealed or sealable cavity 265, which contains at least the space defining the chest cavity but preferably also includes the abdomen cavity. Although not shown, the pilot tubes can exit through or be embedded in sealed portals in the chest wall. By providing a sealed cavity 265 the interaction of the balloons surrounding the airway and the increased intra-cavitary pressure are better demonstrated to the trainee. In addition pressure transducers can be provided within the chest cavity to monitor the pressure generated by CPR and induced by dynamic hyperinflation to improve the understanding of the trainee of the significance of this process. With the sealed embodiment the chest wall 271 and abdominal wall can be constructed of silicone having compliance close to that of the chest wall of the average human and the lungs sized to fill the space of the chest cavity when they are in the resting state. With this sealed embodiment bag inflation of the lungs will therefore increase intra-cavitary pressure, deflect the compliant chest wall outward, the abdominal balloon downward and the abdominal wall outward. It is desirable to provide the ability a seal about the abdomen and chest cavities so that the impact of dynamic inflation is optimally simulated by its effect to reduce lung compliance and displace abdominal cavity 279 anteriorly and inferiorly although these processes will also occur without a sealed system. In the preferred embodiment the anterior chest and abdomen wall of the manikin is clear so that the effects of dynamic inflation can be observed but during the testing CPR trials with the trainees an occluding cover (as for example a silicone skin cover with a Velcro backing) is applied so that ventilation is blind (as it, of course, with normal CPR) in the field.

Although the presently preferred embodiments of this invention have been described, it will be obvious to those skilled in the art that various changes and modifications may be made without departing from the spirit and scope of the invention. Therefor the claims are intended to include all such changes and modifications, which may be made therein without departing form the spirit of the invention. Therefore, the claims are intended to include al such changes and modifications that fall within the true spirit and scope of the invention.

What is claimed is:

1. A method of administering cardiopulmonary resuscitation to a patient, using a system including a disposable stand-alone manual resuscitation bag, and an endotracheal tube adapted to be mounted in the airway, said system further having a flow channel connected with said bag, for connection with said endotracheal tube, said flow channel providing for the flow of air from the bag to said endotracheal tube, into said airway and lung of said patient and, thereafter, from said lung through said airway, tube, and flow channel, said flow channel having an exhalation port in flow communication with said flow channel, the method comprising:
    operatively coupling to said bag, a flow passage comprising an inlet and an outlet, the flow passage including a visual indicator of persistent flow of air exhaled through at least one of said flow channel or said exhalation port, the indicator comprising a readily disposable mechanical flow indicator having a carbon dioxide detector disposed adjacent or within the flow indicator so that air moving within the flow passage is simultaneously passing adjacent the flow indicator and the carbon-dioxide detector, so that both the persistent exhaled flow of air and the absence of exhaled flow of air, wherein the persistent flow of exhaled air has spontaneously ceased in response to a spontaneous end of passive exhalation of air from the patient, are visually detected and are each individually simultaneously viewable with the presence or absence of carbon dioxide in the exhaled air;
    deflating said bag by applying compressive force to said bag to induce flow through said flow channel to inflate said lung,
    releasing said compressive force, said lung passively exhausting said air through said airway, tube and flow channel and out said exhalation port, and
    monitoring said flow using said indicator and adjusting time allowed for exhalation based on said monitoring.

2. The method of claim 1 wherein the indicator of persistent flow is an indicator capable of detecting at least the flow of substantially all air exhaled, the method further comprising monitoring the persistent flow of at least substantially all exhaled air using said indicator and adjusting time allowed for exhalation based on said monitoring.

3. A method of administering cardiopulmonary resuscitation to a patient, using a system including a disposable manual resuscitation bag, the patient having at least one airway and lung, and an endotracheal tube mounted in the airway, said system further having a flow channel connected with said bag, for connection with said endotracheal tube, said flow channel providing for the flow of air from the bag to said endotracheal tube, into said airway and lung of said patient and, thereafter, from said lung through said airway, tube, and flow channel, said flow channel having an exhalation port in flow communication with said flow channel, the method comprising steps of:
    operatively coupling to said bag, a visual flow indicator individually detecting both a persistent flow of exhaled air and absence of flow of exhaled air wherein the persistent flow of exhaled air has spontaneously ceased in response to a spontaneous end of passive exhalation of air, through at least one of said flow channel and said exhalation port,
    deflating said bag by applying compressive force to said bag to induce flow through said flow channel to inflate said lung,
    releasing said compressive force, said lung passively exhausting said air through said airway, tube and flow channel and out said exhalation port,
    monitoring said persistent flow and using said visual flow indicator and adjusting time allowed for exhalation based on said monitoring;
    wherein a flow passage is provided which includes the visual flow indicator, the visual flow indicator comprising mechanical flow sensor, which moves in response to persistent flow, the flow passage having at least one transparent portion and a carbon dioxide detector mounted within said transparent portion, so that exhaled air passes over the carbon dioxide detector at the same time the exhaled air moves the mechanical flow sensor, the carbon dioxide detector being viewable through said transparent portion so that the mechanical flow sensor and carbon dioxide detector are simultaneously viewable by the operator of the bag, the method further comprising;
    disposing said mechanical flow sensor in connection with the bag such that the flow sensor is connected with the bag, and using said mechanical flow sensor, monitoring the persistent flow of air exhaled, and adjusting time allowed for exhalation based on said monitoring.

4. The method of claim 3 wherein said flow channel is disposable and is carried by the bag, the method further comprising the step of; integrating the mechanical flow sensor into the flow channel.

5. The method of claim 3 wherein mechanical flow sensor comprises a rotating wheel, the method further comprising the step of using said rotating wheel, monitoring the persistent flow of air exhaled, and adjusting time allowed for exhalation based on said monitoring.

6. The method of claim 3 further comprising the step of: integrating the mechanical flow sensor into the exhalation port.

7. A portable, stand-alone manual bag system for ventilating a patient during cardiopulmonary resuscitation comprising:
a deflatable bag having a terminal for connection with a source of oxygen;
an air flow channel connected with said bag, for connection with an indwelling endotracheal tube, so that air can flow from the bag into the patient and from said patient through said flow channel;
an exhalation port in flow connection with said flow channel;
a flow passage including a transparent portion and a first visual indicator configured to be mounted adjacent said deflatable bag for receiving exhaled air and detecting both, individually the persistent flow of exhaled air and absence of flow of exhaled air wherein the persistent flow of exhaled air has spontaneously ceased in response to a spontaneous end of passive exhalation of air, into at least one of said flow channel and said exhalation port, the first visual indicator comprising a mechanical flow indicator; and
a second visual indicator comprising a carbon dioxide detector disposed adjacent or within the flow passage so that exhaled air passes adjacent the carbon dioxide detector at the same time the exhaled air passes adjacent said mechanical flow indicator, the carbon dioxide detector being viewable through said transparent portion so both the first visual indicator and the second visual indicator are simultaneously viewable by the operator of the bag so that the operator can readily assess that it is safe to deflate the deflatable bag to administer a breath.

8. The manual bag system of claim 7 wherein said first visual indicator is elastomeric.

9. The manual bag system of claim 7 wherein said second visual indicator is disposed within the flow indicator.

10. The manual bag system of claim 7 wherein said first visual indicator is a pressure indicator.

11. The manual bag system of claim 7 wherein said first visual indicator is mounted adjacent said exhalation port.

12. A device for providing information about a patient during cardiopulmonary resuscitation or transport of a patient by an operator, the device comprising:
an inexpensive and readily disposable flow passage that is configured to connect to a resuscitation bag and to receive exhaled air from a patient;
an inexpensive and readily disposable visual indicator of persistent flow of air disposed in the flow passage, configured to generate an indication of persistent flow and the absence of flow of the exhaled air from the patient, the flow passage having a transparent portion; and
readily disposable carbon dioxide indicator disposed in the flow passage so that exhaled air passes adjacent the carbon dioxide detector at the same time the exhaled air passes adjacent said flow indicator, the carbon dioxide detector being viewable through said transparent portion; and
wherein the visual indication of both the persistent flow of the exhaled air and the cessation of flow wherein the persistent flow of exhaled air has spontaneously ceased in response to a spontaneous end of passive exhalation of air, are visually detected and are each individually simultaneously viewable with the detection of carbon dioxide associated with the exhaled air by said operator so that they may be quickly used together to determine the presence of persistent-exhalation flow or the absence of exhalation flow from the patients lungs after inflation of the lungs by air from within the resuscitation bag during resuscitation or transport of the patient so that the operator can readily determine when it is safe to deflate the resuscitation bag to administer a breath.

13. The device of claim 12, wherein the carbon dioxide indicator comprises a material that changes from a first color to a second color in response to detecting carbon dioxide.

14. The device of claim 12, wherein the flow indicator and the carbon dioxide indicator are coupled to a resuscitation bag.

15. The device of claim 12, wherein the flow indicator is elastomeric.

16. The device of claim 12, wherein the carbon dioxide indicator is disposed within the flow indicator.

17. The device of claim 12, wherein the flow indicator is a pressure indicator.

18. The device of claim 12, wherein the flow indicator is mounted adjacent an exhalation port.

19. The device of claim 12, wherein the flow indicator comprises an object that rotates around a center point, wherein the rate of the rotation of the object indicates the rate of flow of the exhaled air.

20. A device for assisting in the administering of cardiopulmonary resuscitation, the device comprising:
a flow passage to connect to a resuscitation bag, the flow passage to receive exhaled air from a patient;
a flow indicator disposed in the flow passage, the flow indicator to generate a flow output indicating both a first state wherein there is persistent flow of exhaled gas and a second state wherein the persistent flow of exhaled gas has spontaneously ceased in response to a spontaneous end of passive exhalation of air from the patient, the first state and the second state to be each, individually visually detectable; and
a carbon dioxide indicator disposed in the flow passage adjacent the flow indicator, the carbon dioxide indicator to generates an indication responsive to a carbon dioxide value corresponding to a partial pressure of carbon dioxide in the exhaled air from the patient,
wherein a simultaneously viewable combination of the second state and said indication responsive to the carbon dioxide value provides an indication that the patient has transitioned from the first state to the second state corresponding to the end of passive exhalation in which air is not trapped inside the patient's lungs and it is safe to administer a next breath during cardiopulmonary resuscitation.

* * * * *